United States Patent [19]
Carlon et al.

[11] Patent Number: 5,097,212
[45] Date of Patent: Mar. 17, 1992

[54] CELL FOR MEASURING ELECTRICAL CONDUCTIVITY AND ION CONTENT OF VAPOR

[75] Inventors: Hugh R. Carlon, Fallston; Rex M. Pritt, Belair, both of Md.

[73] Assignee: The United States of America as represented by the Secretary of the Army, Washington, D.C.

[21] Appl. No.: 637,029

[22] Filed: Jan. 3, 1991

[51] Int. Cl.$^5$ .................. G01N 27/22; G01N 33/22
[52] U.S. Cl. .................. 324/464; 324/696; 324/703; 324/724; 324/717; 73/61 R; 73/61.1 R
[58] Field of Search .............. 73/61 R, 61.1 R, 155, 73/861.27, 861.28, 861.29, 862.31; 324/464, 696, 703, 724, 717, 72.5; 374/20

[56] References Cited

U.S. PATENT DOCUMENTS

| | | | |
|---|---|---|---|
| 4,425,804 | 1/1984 | Mount | 73/861.28 |
| 4,658,208 | 4/1987 | Lee | 73/61 R |
| 4,854,725 | 8/1989 | Sims | 73/29.03 |
| 4,916,940 | 4/1990 | Mougne | 324/664 |

Primary Examiner—Kenneth A. Wieder
Assistant Examiner—Jose M. Solis
Attorney, Agent, or Firm—Anthony T. Lane; Edward Goldberg; Michael C. Sachs

[57] ABSTRACT

A vapor electrical conductivity cell with sensing plates mounted on insulators exposed to the vapor. Vapor condensation on those insulators cause errors in the conductivity measurements. The improvement of the invention keeps the insulators at a temperature higher than the vapor. The leakage errors are therefore reduced considerably.

9 Claims, 1 Drawing Sheet

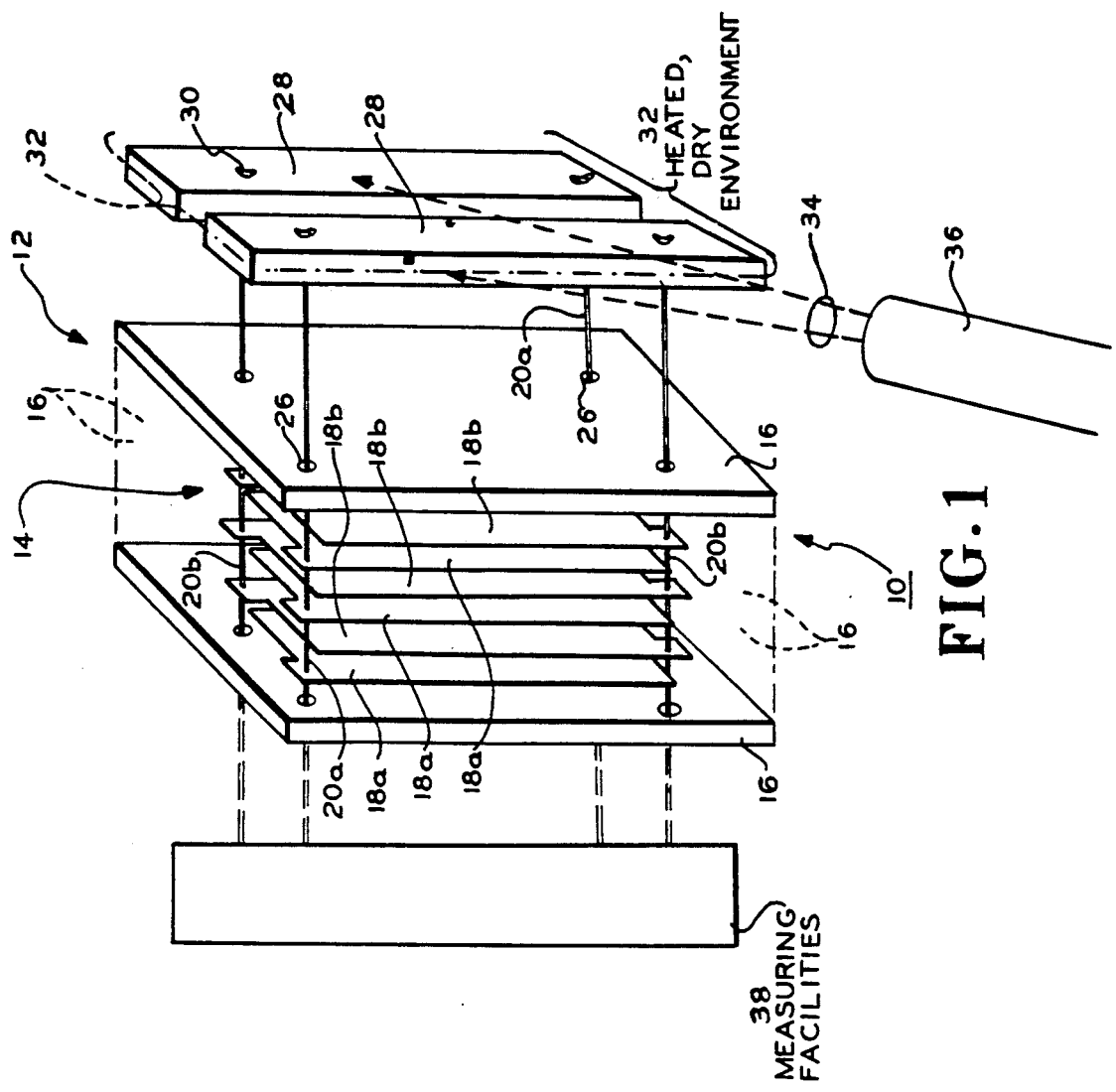
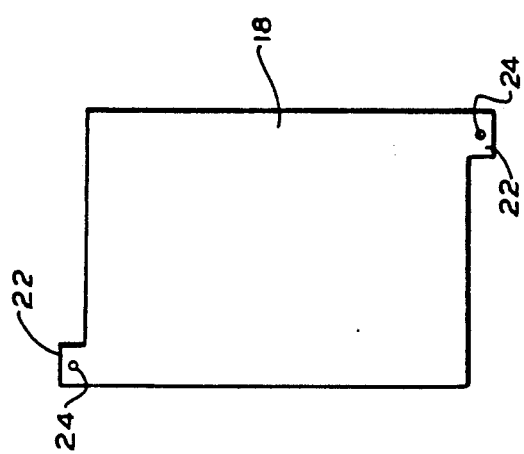

CELL FOR MEASURING ELECTRICAL CONDUCTIVITY AND ION CONTENT OF VAPOR

GOVERNMENTAL INTEREST

The invention described herein may be made, used or licensed by or for the Government for Governmental purposes without the payment to the inventors of any royalties thereon or therefore.

BACKGROUND OF THE INVENTION

The present invention is related to an improved cell for measuring the electrical conductivity and ion content of vapor, and, more particularly, to a cell of this type in which the accuracy of the measurements is increased by reducing or eliminating certain leakage currents.

A typical prior art cell of the above type includes an enclosed volume or chamber within a housing into which a vapor, such as moist air, is introduced. Mounted within the volume is a plurality of metal plates suspended therewithin an adjacent, spaced, parallel relationship. There are two sets of plates.

In a typical cell, each plate in the first plate set, constituting every other plate, is suspended from, and is electrically continuous with, a pair of metal rods or robust wires. One rod passes through each plate of the first set at or near an upper corner thereof, while the other rod passes through each plate at or near a diametric lower corner. The adjacent plates constituting the second plate set are suspended from, and are electrically continuous with, another pair of rods, one of which passes through each plate of the second set at or near an opposite upper corner and the other of which passes through the plates at or near a diametric lower corner.

The foregoing assemblage of plates is suspended within the chamber by mounting the opposite ends of the rods to insulators which are also located in the chamber. The rods are electrically continuous with measuring facilities outside the chamber. After the vapor has been introduced into the chamber, the measuring facilities apply appropriate voltage and current to the rods and the plates and analyze the response of the assemblage to these applied stimuli so as to derive a measurement of the electrical conductivity and ion content of the vapor.

In the past, it has been noticed that the vapor or its constituents at times condense on the insulators. Where the vapor is water vapor or moist air, the condensate on the insulators constitutes a thin water film. Condensates on the insulators permit leakage currents to flow across the insulators. Leakage currents across the insulators affect the measuring facilities so as to obscure or render inaccurate the measurements of the conductivity or ion content of the vapor. Further, if a vapor is to be subjected to successive tests using plates of varying sizes or numbers, insulators of the same size must be used in each test so that the same errors are present in each test to permit meaningful comparisons of the results thereof.

SUMMARY OF THE DISCLOSURE

An object of this invention is the elimination of electrical conductivity measurement errors caused by condensates forming on the insulators used with cells of the above type.

To this end, an improved cell of the above type includes the enclosure, chamber plates, rods, and insulators described above. The improvement includes placing the insulators outside the enclosure and chamber. The rods pass through the enclosure walls and are electrically discontinuous therefrom. This is preferably achieved by forming small holes in the walls large enough to permit the rods to pass therethrough without touching the walls of the holes. The external insulators mount the rod ends extending out of the enclosure to suspend the plates within the enclosure. Facilities outside the enclosure render the insulators vapor- and condensate-free, preferably by maintaining the insulators at a temperature higher than the vapor in the enclosure. This reduces or eliminates leakage currents across the insulators.

The temperature differential between the vapor and the insulators is preferably 10° C. or more, which has been found to reduce leakage currents by a factor of $10^3$ or more. A convenient heating facility is a hot air gun.

BRIEF DESCRIPTION OF THE DRAWING

FIG. 1 is a isometric, partially schematic and partially sectioned view of a cell according to the present invention; and FIG. 2 is a front view of a plate used in the cell of FIG. 1.

DETAILED DESCRIPTION OF ONE EMBODIMENT

A cell 10 for testing the conductivity and ion content of a vapor, such as moist air, is shown in FIG. 1 and includes an enclosure generally indicated at 12 defining and enclosing a volume or chamber 14. The enclosure 12, which is shown only partially to permit viewing the interior thereof, is comprised of walls 16, only two of which are shown; the location of other walls 16 is indicated by broken lead lines.

Suspended in the chamber 14 are a plurality of metal plates 18, assembled in two sets. The plates 18a of the first set are electrically continuous with each other but are electrically discontinuous from the plates 18b of the second set, which plates 18b are electrically continuous with each other. Each set of plates 18a and 18b is suspended in the chamber 14 by a pair of metal rods or wires 20a and 20b. A typical chamber 14 may contain forty plates 18a and 18b which are 26.5 cm square and made of aluminum, each plate 18 being about 0.66 cm from the adjacent plates 18 on either side thereof. The rods 20a and 20b may be stainless steel. FIG. 1 shows only six plates 18a and 18b for illustrative purposes.

As shown in FIG. 2 the plates 18 each include a tab or ear 22 at diametric corners. The tabs 22 contain holes 24 therethrough. To suspend the plates 18a in the chamber 14, the rods 20a are passed through the holes 24 in the tabs 22, with the upper tabs 22 to the left and the lower tabs 22 to the right, as viewed in FIG. 1. The rods 20b are passed through the holes 24 in the tabs 22 of the plates 18b, after the plates 18 of FIG. 2 have been rotated 180° about either axis of symmetry, so that the upper tabs 22 are to the right and the lower tabs 22 are to the left in FIG. 1.

In prior art cells 10, the sets of plates 18a and 18b are suspended in the chamber 14 by insulators which are located within the chamber 14 and which hold the ends of the rods 20. This arrangement, which is not depicted, as it would seem to be evident, suffers from the earlier described disadvantages resulting from the condensation of vapor on the insulators which leads to measurement-perturbing leakage currents thereacposs.

In the cell 10 of the present invention, the rods 20 are extended and pass out of the chamber 14 through holes 26 formed through the walls 16. The holes 26 are large enough so that the rods 20 do not contact and are electrically isolated from the walls 16, yet are small enough so as to effectively confine the vapor within the chamber 14.

The ends of the rods 20 are held in insulators 28 which are wholly outside of the chamber 14. The insulators may be made of any suitable electrical non-conductor, polytetrafluoroethylene being preferred. Only two insulators 28 are depicted these being to the right in FIG. 1, it being understood that two more insulators 28 are intended to be located at the left of the Figure outside of the left-hand wall 16. Any convenient facility 30, such as wing nuts or the like, may be used to mount and hold the rods 20 to the insulators 28. The insulators 28 are themselves mounted in any convenient manner so as to support the plates 18. The size of the holes 26 permits the insulators 28 to support the rods 20 and the plates 18 without the walls 16 performing any support function or having any electrical involvement with the plates 18 or the rods 20.

The insulators 28 are maintained in a vapor-free and condensate-free condition. The insulators 28 may be located in a heated, dry duct or the like, generally indicated at 32, which is outside the walls 16 and does not communicate with the chamber 14 defined by the walls 16 of the enclosure 12. Alternatively, the insulators 28 may be placed a flow 34 of hot, dry air issuing from a device, such as a hot air gun 36 or similar device.

The foregoing results in there being little if any leakage currents across the insulators 28 regardless of the amount or type of vapor present within the chamber 14. The absence of such leakage currents incident to the application to, and measurement of, voltages and currents to the plates 18 by measuring facilities 38 connected to the rods 20, renders more accurate the measurement of the conductivity and ion content of the vapor by the facilities 38. The inventive positioning of the insulators 28 in a benign environment also eliminates variations in errors which can result in successive, tests of the same vapor using plates of varying sizes. Simply stated, the insulators 28 are eliminated from electrical participation in the testing of vapors when the principles of the present invention are followed.

Other embodiments of this invention within the scope of the appended claims will be obvious to the skilled art worker.

What is claimed is:

1. An improved vapor electrical conductivity cell of the type having a volume defined within a walled enclosure; a plurality of planar metal plates within the volume which are maintained in parallel, closely spaced apart relationship by metal rods passing through the plates, every other plate being mounted on and electrically continuous with one of the rods, and adjacent plates being mounted on and electrically continuous with the other rod; and means connected to the rods for measuring the electrical conductivity and ion content of a vapor sample introduced into the volume; wherein the improvement comprises:

means for permitting the rods to pass through, and be electrically insulated from, the enclosure walls;

electrical insulators attached to the ends of the rods outside the enclosure for supporting the rods and the plates within the enclosure; and means for maintaining the insulators at a temperature sufficiently above that of the vapor within the enclosure to render the insulators substantially vapor-free and to substantially reduce leakage currents across the insulators to levels below the leakage currents levels which would exist within the enclosure.

2. An improved cell as in claim 1, wherein:
the permitting means comprises holes through the enclosure walls which are sufficiently larger than the rods to clear and not contact the rods.

3. An improved cell as in claim 1, wherein:
the temperature differential between the enclosure and insulators is about 10° C. or more.

4. An improved cell as in claim 3, wherein:
the leakage current is reduced by a factor of about $10^3$.

5. An improved cell as in claim 1, wherein:
the maintaining means is a heated air source.

6. An improved cell as in claim 1, in which each plate is mounted on two rods, wherein:
the rods pass through tabs on the plates, every other plate having a first tab at one upper corner and a second tab at a diametric lower corner with upper and lower rods passing respectively therethrough, adjacent plates having a first tab at an opposite upper corner and a second tab at a diametric lower corner with upper and lower rods passing respectively therethrough.

7. An improved cell as in claim 6, wherein:
the plates are rectilinear.

8. An improved cell as in claim 1, wherein:
the reduced leakage currents across the insulators are substantially less than the currents which can flow through the vapor.

9. An improved cell as in claim 1, wherein:
the insulators are made of polytetrafluoroethylene.

* * * * *